(12) United States Patent
Stephens

(10) Patent No.: US 7,563,622 B2
(45) Date of Patent: Jul. 21, 2009

(54) MOLYBDENUM COMPLEX AND TEST KIT TO ENHANCE ACCURACY OF ANALYSIS OF ENDOGENOUS ANALYTES IN BIOLOGICAL FLUIDS

(76) Inventor: James Matthew Stephens, c/o Spectrum Laboratories, P.O. Box 8401, Cincinnati, OH (US) 45208

(*) Notice: Subject to any disclaimer, the term of this patent is extended or adjusted under 35 U.S.C. 154(b) by 711 days.

(21) Appl. No.: 10/829,769

(22) Filed: Apr. 23, 2004

(65) Prior Publication Data

US 2005/0239213 A1   Oct. 27, 2005

(51) Int. Cl.
  *G01N 33/53* (2006.01)
  *G01N 33/94* (2006.01)
  *G01N 1/00* (2006.01)
  G01N 33/536 (2006.01)
  G01N 33/543 (2006.01)

(52) U.S. Cl. ............ 436/175; 435/7.1; 435/7.9; 435/962; 436/518; 436/536; 436/537; 436/816; 436/825

(58) Field of Classification Search ............ 435/7.1, 435/7.9, 962, 975; 436/518, 536, 537, 175, 436/816, 825
See application file for complete search history.

(56) References Cited

U.S. PATENT DOCUMENTS 3,963,421 A * 6/1976 Jones .................. 436/162
4,190,496 A * 2/1980 Rubenstein et al. ......... 435/7.9
4,737,456 A * 4/1988 Weng et al. ................ 435/7.92
6,166,187 A * 12/2000 Prusiner et al. ............. 530/419

OTHER PUBLICATIONS

Hori et al., 1977. Formation of colourless molybdate complexes of phosphorus compounds in aqueous solution. J. Inorg. Nucl. Chem. 39: 2173-77.*
ACRO Biotech, 2006. Rapid Urine MDMA Test. pp. 1-2.*

* cited by examiner

*Primary Examiner*—Ann Y Lam
*Assistant Examiner*—James L Grun
(74) *Attorney, Agent, or Firm*—McDonald Hopkins LLC

(57) ABSTRACT

Methods for enhancement in accuracy of immunochemical analysis of heterogeneous biological fluids containing exogenous substances that can interfere in immunochemical analysis for endogenous analytes of interest. According to this method a heterogeneous biological fluid sample is pretreated with an interferant suppression effective amount of a molybdenum coordination complex, so as to reduce manifestation of the presence of said exogenous material under immunoassay conditions. This invention is suitable for the suppression of manifestation of exogenous substances, specifically metabolites of drugs of abuse, during the immunoassay of biological fluids of infants for detection of endogenous substances indicative of a wellness or disease state. This invention also has application for similar suppression exogenous substances in the biological fluid of adults that have been inadvertently exposed to such substances (e.g. secondhand smoke).

2 Claims, No Drawings

MOLYBDENUM COMPLEX AND TEST KIT TO ENHANCE ACCURACY OF ANALYSIS OF ENDOGENOUS ANALYTES IN BIOLOGICAL FLUIDS

BACKGROUND OF THE INVENTION

1. Field of the Invention

This invention relates to a composition, method and test kit. More specifically, this invention is directed to a molybdenum coordination complex, a method for use of such complex in analysis of biological fluids and a test kit for performance of such analysis. This invention is suitable for use in enhancement in accuracy of methods for immunochemical analysis of biological samples obtained from individuals (e.g. newborn infants and nursing infants of drug abusers) that have been inadvertently exposed to substances that can detract from detection of analytes of interest, specifically analytes that are endogenous to biological fluids which are the object of immunochemical analysis.

2. Description of the Prior Art

The diagnostic testing of biological fluids by clinical chemistry and immunochemical analysis is a well established a tool for confirmation of wellness or detection of a disease state. Notwithstanding the wide spread use and acceptance of such tests, the uniqueness of each fluid sample that is subjected to analysis, can introduce potential error into such assays. For example, a lipemic sample can interfere with clinical chemistry analysis by spectrophotometric techniques because of energy losses associated with light scattering from the dissolve fat globules in such samples. Similarly, in immunochemical analysis, the presence of both materials that are endogenous and exogenous to the sample can interfere with either the detection of the analyte of interest, or produce indiscriminate interactions with the test kit reagents and, thus, a false positive or a false negative. These problems have not gone unappreciated either by clinicians or by companies that provide such clinical diagnostic assays.

In virtually all screening assays, the test sample (e.g., blood, urine, saliva, etc.) typically contains some waste materials and cellular matter, along with the analytes of interest. Depending upon the assay format of choice, some isolation (physically and/or optically) of the analyte of interest is required to permit its detection and/or its quantification. The screening assay used in the analysis for such heterogeneous biological fluids generally fall into one of three assay formats/protocols: (a) homogenous assay; (b) heterogeneous assay; and (c) solid phase assay (the latter being further distinguishable as either "immunochromatographic" and "radial partition").

Homogeneous Test Format—In the homogenous assay format, (also commonly referred by the EMIT® trademark for the corresponding commercial product), a sample suspected of containing the analyte of interest, and an analyte mimic conjugated to an enzyme, are admixed, under binding conditions, with a solution containing an antibody specific for binding to an epitope on each of the analyte and analyte mimic/enzyme conjugate. Each of the analyte and analyte mimic/enzyme conjugate compete for available binding sites on the analyte specific antibody. After a suitable incubation period, each of the analyte and analyte mimic/enzyme conjugate arrive at an equilibrium relative to their binding and displacement vis-à-vis the antibody, and, at that juncture, an enzyme specific substrate is added to the mix. The amount of unbound analyte mimic/enzyme conjugate that remains free from association with the antibody retains it enzymatic activity and converts the substrate to a detectable indicator that is measured by standard spectrophotometric analysis. The indicator specifies can be either a chomophore or a flourophore. The relative concentration of indicator detected by such analysis is compared with a standard curve that correlates with the amount of analyte in the test sample.

The foregoing homogeneous test format has been described in U.S. Pat. No. 4,190,496, (issued Feb. 26, 1980, to Kenneth Rubenstein, et al., and assigned to Syva Company), which is herein incorporated by reference in its entirety. Insofar as the performance of such homogenous assay necessarily contemplates the interaction of test kit reagents and sample, and the subsequent measurement of test results within the same fluid environment, the potential for interference from other sample constituents and/or from unreacted test kit reagents, can produce a false or inaccurate results.

For example, in a homogenous assay specific for detection of ethyl alcohol using alcohol dehydrogenase as the reporter enzyme, endogenous dehydrogenase must be initially inhibited with an antibody specific for such endogenous dehydrogenase prior to performance of a homogenous assay for the analyte of interest, See U.S. Pat. No. 5,861,269, Methods For Removing Interferences Due To Endogenous Dehydrogenase In Enzyme Assays (issued Jan. 19, 1999, to McCormack et. al., and assigned to Dade Behring Marburg GmbH). There are also a number other reported instances involving comparable interference, depending upon the analyte and test kit reagent combinations used in such homogenous immunoassays.

Similarly, the use of enzyme specific antibodies have also been reported as necessary to modulate enzyme activity within such homogenous test environments to more accurately correlate such activity with the concentration of the analyte of interest in the test sample, See U.S. Pat. No. 5,972,630, Homogenous Immunoassay Using Enzyme Inhibitors, to Cromer et al. (issued Oct. 26, 1999, and assigned to Dade Behring Marburg GmbH). In the Cromer patent, an enzyme specific antibody and an enzyme labeled conjugate are added to the test sample concurrently. Each of the enzyme specific antibody and enzyme labeled conjugate are capable of binding to the analyte of interest and the enzyme activity of the test medium monitored in the traditional manner.

Solid Phase Test Format—Unlike the EMIT™ type of homogenous assay described above, solid phase enzyme immunoassays effect a physical separation of bound and unbound materials within a test site prior to addition of an enzyme specific substrate for the enzyme labeled conjugate that is bound to such test site. Representative solid phase diagnostic tests, based upon a radial partitioning chromatographic test format, is disclosed in U.S. Pat. No. 4,517,288 (to Giegel et al). In the latter system, the test sample is applied to immobilized binding material within a delimited area of a bibulous membrane. An excess of substrate solution is thereafter applied to this same area, thereby washing (radially displacing) the unbound materials from this delimited area into the surrounding area of the membrane. An indicator molecule is cleaved from the substrate by the immobilized enzyme, is monitored over a defined period of time, and the rate of formation of the indicator compared to a standard curve, which comparison indicates the concentration of analyte in the test sample.

In order to avoid some of the potential problems associated with the use of an enzyme labeled conjugate (e.g. incomplete separation of bound and free conjugate within the test site), a number of solid phase assays have been developed wherein the conjugate is labeled with colloidal gold or other comparable pigment or dye. Thus, as the conjugate is bound to the test site, its concentration at the test site gradually increase, as does the concentration of the colloidal gold, until it becomes visually detectable without further interaction with another test kit reagent (e.g. substrate). Representative solid phase diagnostic tests, based upon a linear chromatographic test format, are disclosed in U.S. Pat. No. 4,703,017 (to Campbell); U.S. Pat. No. 5,591,645 (to Rothstein); U.S. Pat. No. 5,073,484 (to Swanson); U.S. Pat. No. 5,602,040 (to May)—all of which are herein incorporated by reference in their entirety. Notwithstanding, the elimination of a reagent substrate does not otherwise reduce the possible interference from exogenous substances; and, the same physical and immunochemical constraints and limitations apply.

Irrespective of the indicator system, such solid phase immunoassays are not, however, free from interference by either endogenous or exogenous materials that may be present in the test sample. As discussed herein relative to homogenous assays, interferants can compete with test kit reagents to product false positive and thereby result in an elevated or false positive result; or, otherwise inhibit test kit reagents from interaction with the analyte of interest, producing a false negative result. To the extent that these interferants are present, their presence may be manifest by inhibition of the physical separation of bound and free materials within the solid phase, thus, precluding sufficient differentiation of the bound from the free fraction. Where this is inadequate separation of free from unbound materials within the solid phase, it is not possible to effectively measure the presence or amount of analyte at the test site.

The foregoing analytical testing of diagnostic fluids can also be complicated or frustrated by the presence of toxins and/or chemical substances (also "exogenous materials") that have been inadvertently absorbed or ingested by the individual. These toxins or chemical substance typically are converted upon absorption by the body's metabolic processes and, thus, the presence of such toxins or chemical substance is generally manifest by analysis for metabolites of such toxins or chemical substances (also "metabolites" or "exogenous analytes").

Long Felt Need In Prior Art—The exposure of newborn infants in the womb and, thereafter, during nursing, to toxins and chemical agents that are present in its birth mother's circulatory system and breast milk, is an all too common occurrence. Similarly, older individuals are also inadvertently exposed to similar toxins and chemical agents in the ordinary course of going about one's day-to-day life.

In newborns, and nursing infants born to drug abusers, such children often test positive for the drugs that are present within the circulatory system of the birth mother. The presence of such drugs, and the corresponding metabolites of such drugs in the biological fluids of such children, can often interfere with routine medical screening of such children for analytes that are monitored to confirm a wellness state or an abnormal condition associated with childhood development. Similarly, such toxins and chemical agents can be inadvertently inhaled, absorbed through the skin by an adult, or through physical contact with such toxins and agents and/or consumed orally incident to sharing a drink or dinner ware utensils. Moreover, the individual experiencing such exposure is often unaware such event or contact. This is particularly common in social settings, and in contacts with individuals that are relative strangers to one another. For example, it is not uncommon to attend a concert or a night spot and be exposed to second hand smoke from a controlled substances, such as marijuana and/or cocaine; or, to share a glass or a cigarette with a stranger in such social settings that may have been similarly contaminated with a controlled substance.

The amount or duration of an individual's contact with such toxins or agents need not be extensive for absorption to occur. Moreover, depending upon the circumstances surrounding such contact, such transient exposure can result in the appearance of the toxin or agent and/or metabolites thereof in the biological fluids of the person having undergone such inadvertent exposure. Notwithstanding that such exposure is brief, and the effect thereof is not overtly manifest, the presence of compounds indicative of such toxins and agents within the biological fluids of an individual, can have both medical, social and legal consequences.

For example, the limited and inadvertent exposure to relatively small amounts of second-hand smoke from a marijuana cigarette can result in metabolites (cannabinoids) remaining in tissues within the body for an extended period of time, and because of the sensitivity of current clinical chemistry analysis and immunodiagnostics, the presence of such compounds can be manifest in the analysis of biological fluids from such individuals for up to thirty (30) days following such exposure.

Typically, an analysis of biological fluids for endogenous analytes of interest in children and adults can be performed upon anyone of a number of different biological specimens and, in certain instances, upon extracts of samples of hair from such individuals undergoing such testing. The biological fluids of choice for performance of a screening analysis are generally obtained by non-invasive techniques; and, such fluids can include urine, saliva and/or a transudate (an interstitial fluid extracted through the skin). Where hair is the "sample" of choice, the living root from the hair strand is extracted and the extract thereof subjected to analysis. Alternatively, invasive methods can also be used to obtain a biological fluid (e.g. blood) for analysis. The venous and capillary blood samples obtained for this purpose are initially separated into their various fractions (cellular and plasma), and the plasma fraction subjected to further processing/dilution and analysis.

Heterogeneous Biological Fluid Samples—In each instance the sampling technique, as described herein, is indiscriminate as to its ability to confine the content of the sample to only those endogenous analytes of interest, or to the exclusion of compounds that can interfere with accurate detection and measurement of the endogenous analytes of interest. Thus, in the analysis of biological fluid samples and extracts from human tissues for analytes that are endogenous to body, the immunoreagents used therein can also interact compounds (metabolites) indicative of toxins and chemical agents that may have been inadvertently inhaled, absorbed through contact with the skin or ingested by the individual subjected to such testing. Where the biological fluid of choice is a waste material (e.g. urine, feces, etc.) produced by the individual's body, the presence of such toxins, chemical agents and/or their corresponding metabolite, (also "exogenous materials"), is most likely to occur. Conversely, where the fluid is an excretion from an organ or gland (e.g. saliva) the likelihood of interference of from an exogenous material is reduced. The analysis of venous and/or capillary blood tends to suffer from the same type of contamination as samples of human waste.

Where metabolites and/or compounds indicative of such toxins and chemical agents are present in the test sample of the biological fluid sample or tissue extract, such compounds may, in the subsequent analysis of such test sample, either (a) mask the presence of one or more of the endogenous analytes of interest by interacting with an analyte of interest, and thereby produce a false negative; (b) interfere with test kit reagents used to detect the endogenous analytes of interest and thereby produce a false negative; and/or (c) mimic the endogenous analyte of interest and thereby produce a false positive or an artificially elevated level of the analyte above the basal level for the analyte of interest within the sample. In each instance, the test result obtained does not accurately reflect the status of an individual's disease or wellness state, and can result in misdiagnosis of the individual that is undergoing such testing. In addition to the obvious medical consequences of an erroneous test results for such endogenous analyte of interest, such test may also manifest the presence of the compound indicative of exposure to a toxin or chemical substance, and, under certain circumstance, a produce a positive drug test.

In social terms, the positive testing for drugs of abuse from inadvertent exposure to second hand smoke can be devastating professionally, and, in addition, result in social/legal consequences that may never be resolved or purged from an individual's employment or criminal record.

As is evident from the foregoing discussion, there continues to exist a need to selectively isolate endogenous analytes within a test sample from toxins or chemicals, or metabolites of toxins or chemicals, that can potentially interfere with detection of such endogenous analytes. In order to be effective, the materials and methods used in such isolation cannot otherwise interfere with either the test kit chemistries or the test protocol or, in automated systems, the performance of the test instrument (e.g. test cycle time, reading of a reagent blank, reading of sample optical interferants, etc.), used in the detection of the endogenous analytes of interest.

OBJECTS OF THE INVENTION

It is the object of this invention to remedy the above as well as the related deficiencies in the prior art.

More specifically, it is the principle object of this invention to provide a composition that is effective to diminish the manifestation of the presence of exogenous compounds in the clinical and immunochemical analysis of biological fluids.

It is another object of this invention to provide a molybdenum coordination complex, for use in clinical analysis of analytes that are endogenous to a biological fluid sample.

It is another object of this invention to provide a molybdenum complex, to diminish the manifestation of the presence of exogenous compounds, in the clinical and immunochemical analysis of biological fluids for endogenous analytes of interest.

Additional objects of this invention include the inclusion of a molybdenum complex within a test kit and method for analysis of biological fluids wherein such analysis results in a diminished manifestation of the presence of exogenous compounds.

SUMMARY OF THE INVENTION

The above and related objects are achieved by providing a composition containing a molybdenum complex, and contacting such complex under assay conditions, with a test sample containing an exogenous substances, associated with toxin or chemical agent. The precise mechanism of operation of the molybdenum complex is not known, however, it is hypothesized that the molybdenum complex interacts with exogenous substances within the sample, specifically, with metabolites that may be present in biological fluids that are indicative of each of marijuana and cocaine, thereby preventing the manifestation of their presence within the biological fluid under assay conditions.

The amount of molybdenum complex added to the sample is based upon an empirical testing of such complexes relative to a standard solution or calibrator, thereby determining the ability of a particular complex to inhibit the manifestation of an endogenous materials believed, or known, to be present in the sample. In, for example, the analysis of a biological sample believe to contain tetrahydrocannabinol (THC), generally the interaction of from about 0.05 to about 0.50 mM of molybdenum complex with THC in the biological sample is effective to suppress the manifestation of the presence of THC during immunochemical analysis of the sample for endogenous analytes. A comparable proportion of molybdenum complex is effective to suppress the manifestation of the presence of benzileganine during immunochemical analysis of the sample for endogenous analytes. In each instance, the endogenous analytes within the sample appear to be substantially unaffected and, thus, their detection and measurement provides an accurate depiction of a wellness or a disease state.

DETAILED DESCRIPTION OF INVENTION INCLUDING THE PREFERRED EMBODIMENT

The medical, social and forensic implications of inadvertent exposure to a controlled substance cannot be overstated. For example, the presence of metabolites of drugs of abuse in biological fluids samples of infants may depress or mask an elevated level of the analyte, such as bilirubin, and thus conceal liver malfunction in such infants. It is believed that the addition of molybdenum complex to biological fluid samples is not only compatible with the screening analysis for common analytes associated with infant metabolic imbalances and disease, but also the clinical testing for the more common indicia associated with detection/monitoring of an individual for pregnancy (HCG), diabetes (Insulin) and infectious diseases (HIV).

As above noted, the routine analytical testing of biological fluids provides a screening tool for determining the presence or level of analytes, indicative of wellness or disease states, that may be present in a test sample (also "endogenous analytes"). It is further appreciated that such diagnostic testing is not without its technical and social problems. For example, the accuracy of such testing can be complicated or compromised by the presence of toxins and/or chemical substances that have been inadvertently absorbed or ingested by the individual. These toxins or chemical substance are typically converted upon absorption into the body by metabolic processes and, thus, the presence thereof manifest by the presence of metabolites corresponding to such toxins or chemical substances.

The instant invention utilizes a molybdenum coordination complex to diminish the manifestation of such toxins and chemical substances, including the metabolites thereof, during the performance of analysis of biological fluids.

Analytical Test Formats—In a homogenous enzyme immunoassay of the type commonly used in screening of biological fluids, (e.g. Syva EMIT® enzyme immunoassay), freeze dried test kit reagents are first reconstituted with a buffer provided for this purpose. Thereafter, an aliquot of sample, that has been conditioned with molybdenum complex in the manner described above, is admixed with an antibody solution of the test kit, and analyte within the sample permitted to interact with the antibody in such solution. After a suitable incubation period, an analyte mimic/enzyme conjugate is contracted with the reaction mixture; and, such conjugate competes with the analyte in the sample for the available binding sites on the antibody in the mixture. Upon establishment of a competitive equilibrium between the analyte and analyte mimic/enzyme conjugate for the available binding site of the antibody, an enzyme (chromogenic or flourogenic) substrate is added to the test environment, and the rate of production of an indicator (chromophore or flourophore), derivative from enzymatic cleavage of the substrate, monitored over a defined period of time by the instrumentation that has been precalibrated for the measurement of such indicator. The rate of formation of the indicator, typically a flourophore, is compared to a standard curve for this same indicator, and the concentration of the analyte within the urine sample determined thereby.

Where the biological fluid sample is, for example, whole blood (herein also "heterogeneous sample"), the sample typically includes cellular matter, proteins, sugars, salts, and various other chemical compounds. In order to minimize interference or, alternatively, to enhance differentiation of the constituents within the test sample from one another, the analytical protocols, used in the analysis thereof, require a degree of physical separation of the sample constituents from one another, either prior to or concurrent with performance of the diagnostic testing. This separation can be performed prior to analysis by filtration or chromatographic techniques, or, as is most common, concurrent with application of an aliquot of the test sample to solid phase of the test strip or contact of the test sample with the test medium (.e.g. coated beads or magnetic particles). Within the context of this invention, the phrases "test medium" or "test strip" or "solid phase" is indicative of membrane or bibulous synthetic or natural filter medium having either a uniform or asymmetric structure capable of support chromatographic migration of biological fluids, and the separation thereof from particulates that may also be present in such fluids. In certain instances magnetic particles or micro beads coated with an immunoreagent are also used in combination with a membrane or bibulous synthetic or natural filter medium, and, thus, are also included within phrase "solid phase".

In a representative construct of a simple screening diagnostic test, a linear test strip can be initially prepared having three defined area: one end thereof is engineered to collect a heterogeneous sample, an intermediate section designed to transport a fluid fraction of the sample by capillary action to a delimited area upstream of the sample collection area. After the sample contacts this delimited area, the sample continues to migrate along the intermediate section to a bibulous pad at the other end thereof. The fluid capacity of the test strip is, thus, defined or limited by the void volume of the collection pad, intermediate section and the bibulous pad; and, thus, the concentration of endogenous and exogenous substance subject to contact with the test kit chemistries also limited proportionally.

This delimited area, within this intermediate section of the test strip, typically includes an immobilized binding material for capture of either a test kit reagent/analyte complex or a test kit reagent that mimics the analyte of interest. The capture of either of these entities can in and of itself can be manifest by the appearance of a colored material (e.g. colloidal gold). Alternatively, if one of the substances captured within the test site is, for example, an enzyme, a substrate specific for the enzyme can thereafter be contacted with the test site, to produce a color indicative of the presence of the analyte at the test site, or, an elevated level of the analyte at the test site, (e.g. pregnancy test).

This process of separation of the various constituents of a heterogeneous biological sample from one another can be accomplished in automated systems in similar fashion by radial partitioning of the sample within a solid phase (Test Tab); that is by coincident application of the sample and test kit reagents to a delimited area of the solid phase having an immobilized binding material, and washing unbound materials from the delimited area by means of application of a wash fluid or substrate wash.

In a typical screening assay for drugs of abuse, the diagnostic test device can include a multiple or a central sample collection pad coupled with means for distribution of the sample to a panel of analyte specific tests within the test device. A fluid sample distribution system suitable for use in a multi-test diagnostic panel is disclosed in U.S. Pat. No. 6,203,757, issued to Lu, et. al., which is herein incorporated by reference in its entirety. A typical multi-panel diagnostic test device having the foregoing configuration can be used in the screening of infants and young children for certain analytes or disease states; or, alternatively, in the screening of employees for drugs of abuse.

Molybdenum Complexes—The phrase "molybdenum complex" or "molybdenyl complex" or "molybdenum coordination complex" as used herein are intended to describe a three dimensional coordination complex having from about 5 to about 12 molybdenyl metal ions covalently bonded to one another through oxygen atoms; and, in the preferred embodiments of this invention, such coordination complex also includes a Lewis acid to enhance the stability thereof. The coordination complexes of this invention have a net negative charge relative to the exogenous substance with which they interact.

Thus, when such complexes are present within biological fluids they can and do become associated with relatively positive compounds and materials, such as metabolites of toxins and chemical substances, (e.g. drugs of abuse); and, thereby render such metabolites effectively neutral vis-à-vis immunochemical interaction that are designed for detection of endogenous analytes of interest. It is hypothesized that the interactions of the molybdenum complexes with exogenous materials in the test sample effectively neutralizes the exogenous materials relative to potential interactions with endogenous analytes of interest and/or reduces the affinity of test kit reagents and exogenous materials to one another, or a combination of the two. Irrespective of the mode of action such interactions effectively diminish and/or neutralize potentially interference with detection of the analytes of interest.

The molybdenum complexes suitable for use in this invention have been previously described in the open literature, and/or can be prepared in accordance with techniques described in the open, See for example Hori, T., *Formation Of Colorless Molybdate Complexes Of Phosphorous Compounds In Aqueous Solution*, J. Inorg. Nucl. Chem. (1977), Vol. 39, pages 2173-77; Saha, H. K., et al., *Chemistry Of Oxometal Ions IX. Studies On Molydenyl Phosphates*, J. Inorg. Nuc. Chem. (1975) Vol. 37, pages 840-41 As is evident from the foregoing articles, these molybdenum complexes can be prepared by conventional laboratory techniques using readily materials and equipment. To the extent necessary and/or appropriate these technical papers are herein incorporated by reference in their entirety.

The preferred molybdenum complexes suitable for use in this invention include oxo molybdenum complexes such as molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable molybdenum complexes include hydroxo derivatives derived from, for example, glycerol, tartaric acid, and sugars.

In one of the preferred embodiments of this invention, the molybdenum complex is added to the biological fluid sample prior to the analysis thereof. The phrase "molybdenum complex" is inclusive of a heterocyclic poly acid complex of molybdenum and an oxyanion, such as phosphomolybdic acid. The preferred molybdenum complexes suitable for use in this invention include the molybdenyl phosphates, specifically, molybdenyl acidtriphosphate—$MoO(H_2PO_4)_3$; molybdenyl trimetaphosphate—$MoO(PO_3)_3$; oxo-μ-oxodi (dihydrogen phosphate)molybdenum—$Mo_2O_3(H_2PO_4)_4$; and any combination and mixtures thereof.

The molybdenum complex of choice are formed of molybdate ($MoO_3$) and a phosphorous oxyanion, is dissolved in a buffered solution (e.g. PBS) at a concentration in the range of from about 0.01 to about 0.10 weight percent. The stock solution is then combined with the biological fluid sample to form a fluid mixture wherein the stock solution comprises about 5 to 10% by volume. Thus, the molybdenum complex is present in the sample in the range of from about 0.005 to about 0.001 weight percent, or $5 \times 10^{-6}$ to $5 \times 10^{-3}$ mM.

The most preferred molybdenyl complexes suitable for use in this invention are described by Hori in the foregoing article, specifically, molybdenyl phosphates, specifically, molybdenyl acid triphosphate—$MoO(H_2PO_4)_3$; molybdenyl trimetaphosphate—$MoO(PO_3)_3$; oxo-μ-oxodi (dihydrogen phosphate) molybdenum—$Mo_2O_3(H_2PO_4)_4$; and any combination and mixtures thereof.

Test Kit Reagents—Within the context of this invention, the test kit of this invention can contain one or more molybdenum complexes capable of interaction with exogenous substances, such as toxins or chemical substances or a metabolite of a toxin or chemical substance. As above noted and once again emphasized, the interactions contemplated herein include inducing conformational changes in the exogenous material, and/or covalent bonding between the exogenous material and the molybdenum complex and/or electrostatic association (van der Wall forces) between the exogenous substance and the molybdenum complex. In the preferred embodiments of this invention, the effect of the molybdenum complex interactions with the exogenous substance is to diminish, and most preferably, neutralize the manifestation of the presence therein. It is understood that the presence of such exogenous substances can be manifest by means of interaction thereof with a test kit reagent specific for interaction with an analyte that is endogenous to the test sample or, alternatively, with a test kit reagent having affinity for the exogenous substance. In either instance, the addition of a molybdenum complex to the sample containing the exogenous substance causes the exogenous substance to change in its immunochemical signature in some undefined way, and thereby no longer exhibit the same characteristic immunochemical signature (epitope) that identified it as the exogenous substance.

Mechanism—Within the context of a homogenous enzyme immunoassay, the interactions contemplated herein between the exogenous materials and the molybdenum complex, are believed to reduce the affinity between the exogenous materials and the analyte specific antibody of the test kit, thereby suppress the manifestation of expression of the exogenous within the such assay, without effecting the ability to determine the presence of endogenous analytes that are present in the test sample.

Likewise, within the context of a solid phase assay, the separation of analytes of interest from heterogeneous biological fluid samples remain unaffected by the interaction of the exogenous materials and the molybdenum complex. Thus, upon the chromatographic movement of a heterogeneous fluid test sample within a solid phase, the movement of larger molecules, proteins and the complex migrate slower within the solid phase than small molecules, thereby effecting the desired spatial distribution thereof within the solid phase test medium. This spatial distribution is time dependent and thus in order to take advantage of such inherent differences in mobility, most test protocols require both an incubation period to elapse before reading the test results within the test zone, and the termination of the testing after a defined period of time has elapsed. Within the context of this invention, the interaction of the molybdenum complex with the exogenous materials in the sample, is believed to reduce the mobility of such exogenous substances within the solid phase, and thereby to inhibit migration of such exogenous substance to the test site, or alternatively so modifies the exogenous substance that the immunochemical signature thereof (e.g. epitope or access of epitope to test kit reagent), is no longer recognized by the immobilized test kit reagents within the test zone. In either case, the manifestation of the presence of such exogenous substance is substantially diminished or entirely neutralized, so as to better differentiate the endogenous analytes of interest in the test sample. Accordingly, in the concurrent analysis of a biological fluid for a panel of analytes, any exogenous substances that may be present therein, are effectively partitioned within the solid phase, or physically confined by their size or migrational patterns to a portion of the test medium remote from the test site that is specific for the endogenous analytes within the test sample. This isolation or confinement permit improved differentiation of the analytes of interest from interfering substances that are also present in the test sample.

Efficacy—The invention has application in the diagnostic testing of biological fluids from newborn infants and more senior individuals who have been inadvertently exposed to toxins and chemical substance, the presence of which could potentially interfere with diagnostic analysis for analytes indicative of disease or wellness state. The invention has particular application to diagnostic testing of biological fluids by homogenous enzyme immunoassay, and sold phase based diagnostic test formats utilizing immunochromatographic techniques to isolate an analyte from other sample constituents within a test site.

Safeguards—Although the use of the molybdenum coordination complex of this invention is potentially subject to misuse by an individual attempting to avoid detection of drugs of abuse, confirmation testing of such sample shall readily reveal the presence of the molybdenum coordination complex because of the metallic component of this coordination complex. Accordingly, the benefits of this invention to the medical diagnostic community far outweighs any possible misuse by the drug abuser.

EXAMPLES

The Examples that follow further define, describe and illustrate a number of the preferred embodiments of this invention. Parts and percentages appearing in such Examples are by weight unless otherwise indicated. Apparatus and equipment used in both the synthesis and the evaluation of the materials are standard or as hereinbefore described.

Example I

A urine sample including marijuana and cocaine is analyzd. The sample is initially filtered to remove particulate matter, and thereafter separated into two (2) 1 ml aliquots. One aliquot of sample is pretreated with 0.1 mls of a 0.5 weight percent solutions of molybdenyl acidtriphosphate while the other do not receive similar treatment. Each aliquot of sample is, thereafter, subjected to homogenous immunoassay for measurement of bilirubin, in accordance with standard laboratory procedures. In the sample that did not receive the molybdenum complex pretreatment, the bilirubin content thereof was below the normal endogenous range. In contrast to this result, the sample receiving the molybdenum complex pretreatment was somewhat elevated.

Example II

The procedures of Example I are repeated except for the substitution of the following molybdenum complexes for molybdenyl acidtriphosphate of Example 1:
 molybdenyl trimetaphosphate—$MoO(PO_3)_3$;
 oxo-µ-oxodi(dihydrogen phosphate)molybdenum—$Mo_2O_3(H_2PO_4)_4$; and
 an equimolar mixture of molybdenyl trimetaphosphate—$MoO(PO_3)_3$ and oxo-µ-oxodi(dihydrogen phosphate) molybdenum—$Mo_2O_3(H_2PO_4)_4$.

Example III

The procedures of Example I are repeated except the samples are subjected to analysis for antibodies to HIV. The aliquot pretreated with the molybdenum complex tested positive for the antibodies to HIV, whereas the test results for the untreated aliquot were inconclusive.

Example IV

Two (2) aliquots of urine are prepared in accordance with the procedures of Example I, and thereafter subject to analysis by radial partition immunoassay for measurement of HCG. The pretreated sample produced an elevated level of HCG, whereas the untreated sample was inconclusive for the presence of HCG.

Although this invention has been primarily described in terms of specific examples and embodiments thereof, it is evident that the foregoing description will suggest many alternatives, modifications, and variations to those of ordinary skill in the art. Accordingly, the appended claims are intended to embrace as being within the spirit and scope of invention, all such alternatives, modifications, and variations.

What is claimed is:

1. An immunoassay method to detect an analyte endogenous to a biological fluid sample wherein said sample also contains an exogenous material selected from the group consisting of cannabis, cocaine, and derivatives thereof capable of interfering with detection and measurement of said endogenous analyte in said fluid sample, comprising the steps of:

A. Obtaining said biological fluid sample from an individual who has been exposed to said exogenous material, or a metabolite of said exogenous material, capable of interfering in analysis of said fluid for said endogenous analyte;

B. Pretreating said biological fluid sample with an interferant suppression effective amount of a molybdenum complex to reduce manifestation of the presence of said exogenous material under assay conditions for said endogenous analyte without removing said exogenous material or said metabolite of said exogenous material from said biological fluid sample, said molybdenum complex formed from a molybdate compound and an oxyanion of phosphoric acid and present in said sample at a concentration of from about $5 \times 10^{-6}$ to $5 \times 10^{-3}$ mM; and C. Subjecting said fluid sample of Step (B) to immunoassay for said endogenous analyte.

2. The method of claim 1, wherein the molybdenum complex is selected from the group consisting of molybdenyl acidtriphosphate—$MoO(H_2PO_4)_3$; molybdenyl trimetaphosphate—$MoO(PO_3)_3$; oxo-µ-oxodi(dihydrogen phosphate) molybdenum—$Mo_2O_3(H_2PO_4)_4$; and any combination and mixtures thereof.

* * * * *